United States Patent [19]
Cooper et al.

[11] Patent Number: 5,319,959
[45] Date of Patent: Jun. 14, 1994

[54] AIR LUBRICATED PENETROMETER ROD SYSTEM

[75] Inventors: Stafford S. Cooper; Philip G. Malone, both of Vicksburg, Miss.; Gregory D. Comes, Fort Collins, Colo.

[73] Assignee: The United States of America as represented by the Secretary of the Army, Washington, D.C.

[21] Appl. No.: 961,803

[22] Filed: Oct. 16, 1992

[51] Int. Cl.$^5$ .............................................. G01N 3/00
[52] U.S. Cl. .............................................. 73/84; 73/9
[58] Field of Search ................ 73/9, 84, 786; 175/21, 175/40, 50, 227, 228

[56] References Cited

U.S. PATENT DOCUMENTS

| 845,120 | 2/1907 | Raymond | 175/21 |
| 848,395 | 3/1907 | Raymond | 175/21 |
| 4,499,954 | 2/1985 | Diggle | 73/84 |

OTHER PUBLICATIONS

"Site Characterization Using the Cone Penetrometer Test", Olsen et al., ASCE Specialty Conference, Use of Insitu Testing in Geotechnical Engineering, Jun. 22-25, 1986.

"Soil Classification and Site Characterization Using the Cone Penetrometer Test", Olsen et al., First International Symposium on Penetration Testing, Mar. 20-24, 1988.

"Standard Test Method for Deep Quasi-Static, Cone and Friction-Cone Penetration Tests of Soil" ASTM D 3441-86.

*Primary Examiner*—Robert Raevis
*Attorney, Agent, or Firm*—Luther A. Marsh

[57] ABSTRACT

An air or gaseous fluid lubricated penetrometer reduces friction between the soil and the push rod string. Air is pumped into the interior of the string and is directed by exit ports into the annular space between the soil and the outer walls of the string. Without damaging the soil, the air prevents the soil from adhering to the sides of the string and thereby reduces frictional forces that restrict the downward movement thereof. The exit ports in the string are located above the instrument housing so that accurate measurements can be made on the soil properties.

13 Claims, 5 Drawing Sheets

AIR LUBRICATED PENETROMETER ROD SYSTEM

BACKGROUND OF THE INVENTION

This invention relates to a cone penetrometer system for conducting a Cone Penetrometer Test (CPT). In particular, the invention is directed to an apparatus for lubricating the push rod portion of a cone penetrometer upstream of the instrumentation package to thereby improve measurement accuracy and test depth without damaging the soil.

The so-called Cone Penetrometer Test (CPT) has been used to classify soils and characterize sites in various applications including, for example, dam construction and maintenance and other major construction projects. See for example, "Site Characterization Using the Cone Penetrometer Test", Olsen et al., ASCE Specialty Conference, Use of In-Situ Testing in Geotechnical Engineering, Jun. 22–25, 1986 and "Soil Classification and Site Characterization Using the Cone Penetrometer Test", Olsen et al., First International Symposium on Penetrometer Testing, Mar. 20–24, 1988. The standard equipment and methodology is described in "Standard Test Method for Deep Quasi-Static, Cone and Friction-Cone Penetration Tests of Soil" ASTM D 3441-86.

In General, the cone penetrometer test data may be analyzed to provide information on soil strength and soil classification. CPT data can be normalized with respect to vertical effective stress for comparison of data from various depths in soil.

The typical CPT test, as performed in the United States, is illustrated in FIG. 1 and generally comprises pushing a known 3.57 centimeter diameter electrical CPT probe 10 into the earth 11 at 2 cm/sec using one or more interconnected 1 meter hollow push rods 12 in a string 13 driven with the reaction force of a large mass such as a truck 14. The probe 10 includes an instrument housing 16 at the distal end 18 of the push rod string 13. A conical tip 20, connected to the housing 16, penetrates the earth. A tubular section of the penetrometer, called the friction sleeve 21, is located directly above the cone tip 20, but it is physically separated from it. A cone support 23 connects the tip 20 to the instrument housing 16. The friction sleeve 21 surrounds the cone support and carries one or more sensors, e.g. strain gauges 25, forming a load cell 27 there-in. The sensors measure local side friction resistance developed between the friction sleeve 21 and the surrounding soil 11 independently of the force exerted on the tip 20. Devices (not shown) in the instrumentation package 16 are responsive to the sensors and are coupled to equipment in the truck 14 by means of wires 22 which run up to the surface inside the string 13 of the hollow push rods 12.

Generally two measurements are recorded, namely, cone resistance $q_c$ which is an end bearing stress and sleeve friction resistance $f_s$, which is a localized large-strain index of sheer strength. Both measurements are usually reported in terms of tons per square foot (tsf) although metric units may also be used if desired.

In the past, the metal penetrometer rod was forced into the soil with no lubrication. The depth of penetration is determined by the point in which the point penetration resistance and the total side wall friction resistance equal the weight of the reaction mass (typically 20 tons) being used to drive the penetrometer into the ground. This system is inefficient because the total side wall friction on the rod sections 12 in the ground 11 quickly limits the depth of penetration even when the tip resistance is low. Some penetrometers have been built with ports for ejecting drilling mud 32 into the area between the string 13 and the soil 11. However, these units are complicated and cumbersome to use because of the problems associated with the handling of drilling mud and the mud injection system. More importantly, however, drilling mud under pressure can cause damage or fracture 34 the soil 11. Fractures 34 are unacceptable, especially if a test is performed at a dam site where such damage may propagate. Finally, drilling mud is dangerous and difficult to clean up because it creates slippery surfaces.

SUMMARY OF THE INVENTION

The present invention eliminates and obviates the disadvantages and limitations of described prior arrangements. In accordance with the invention, air or gaseous fluid lubricated penetrometer permits deeper penetration of the instruments into the soils by reducing friction between the soil layers being penetrated and the sides of the push rods. In one embodiment, air is directed into the interior of the push rod and is allowed to exit gas ports near the end of the rod string into the annular space between the sides of the rod and the surrounding soil. Air under pressure moves upwardly towards the ground surface along the annular space around the push rod and has the effect of preventing the soil from adhering to the side of the rod and thereby reduces frictional forces that restrict the downward movement of the push rod. The exit ports in the rod are located above the instrument housing of the penetrometer so that accurate measurements can be made on the soil properties. Air lubrication is thus provided only on the upper part of the rod and, therefore, does not interfere with the instrument readings.

In a particular embodiment, an air lubricated penetrometer has a tip for penetrating the soil and an instrument housing is axially secured to the proximate end of the tip for sensing soil conditions thereat. A penetrometer push rod having one or more sections has a free end axially secured to the proximate end of the instrument housing for transferring a penetration force axially applied to the proximal end of the push rod to the penetrometer tip through the instrument housing. Means is provided for introducing a gaseous fluid into the rod and the free end of the penetrometer push rod has a plurality of gas exit ports for carrying the gaseous fluid to a space formed about and along the push rod from above the instrument housing to the surface. The gas or air flows upwardly and has no significant effect on the soil or the instrument readings as the penetrometer is urged forward in the soil.

DESCRIPTION OF THE INVENTION

Figure 1:
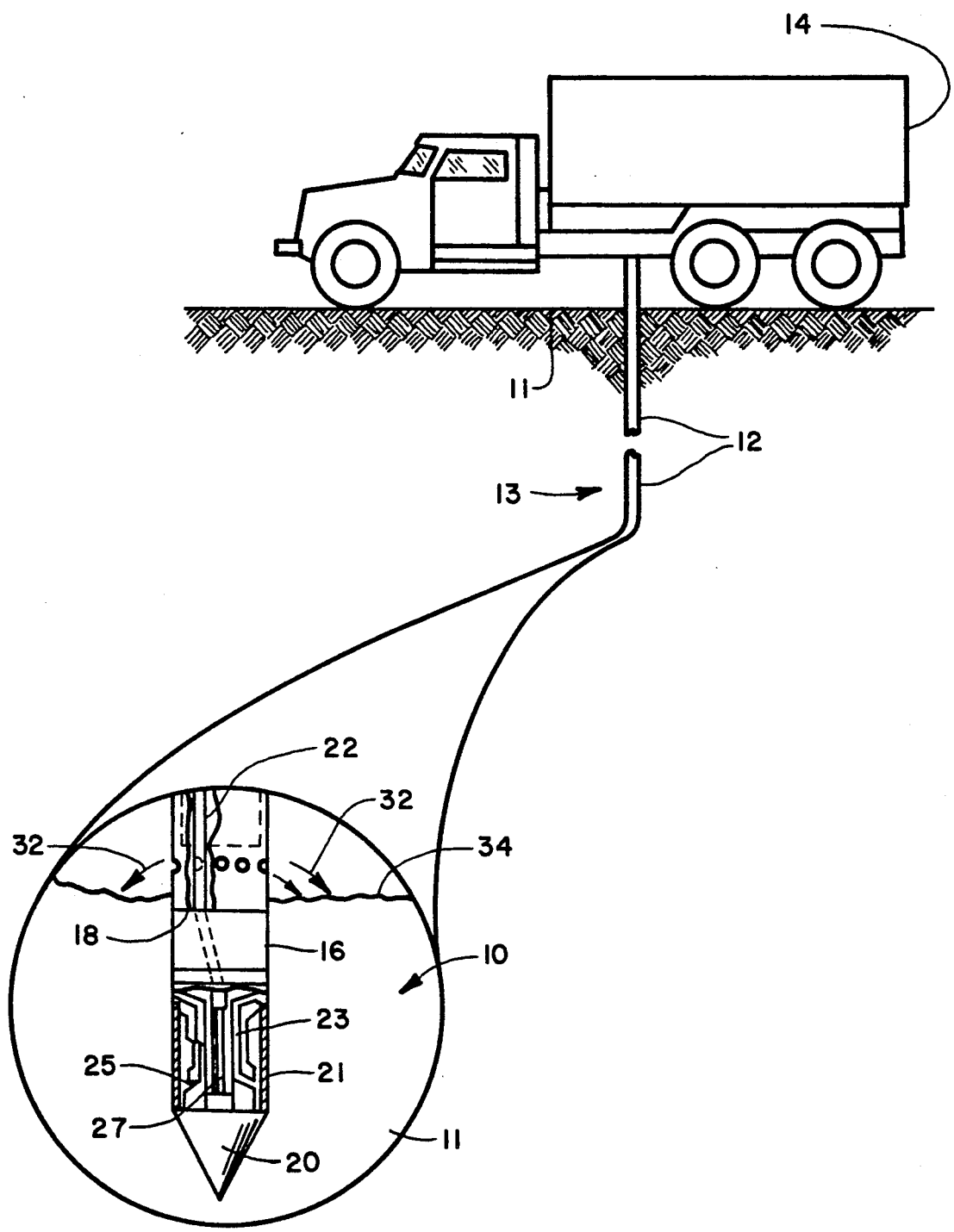
FIG. 1 is a schematic representation with an enlarged portion illustrating a known penetrometer system.
Figure 2:
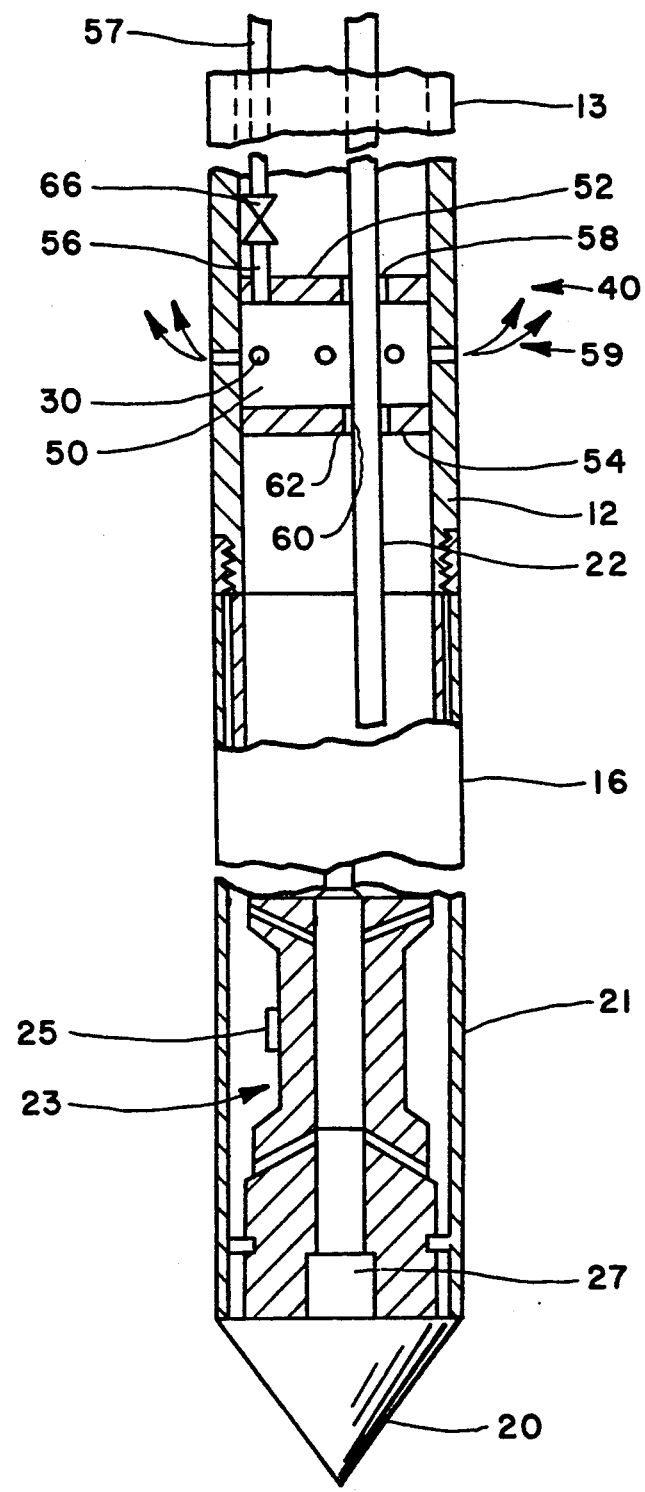
FIG. 2 is an enlarged fragmentary side sectional elevation illustrating a portion of an air lubricated penetrometer push rod, an attached instrument section and a tip.

FIG. 2 illustrates in a fragmentary side sectional elevation an embodiment of the present invention for an air lubricated penetrometer system 40. The portion shown corresponds to a similar portion in the enlargement of FIG. 1 but incorporates the improvements of the invention. In particular, the air lubricated penetrometer system 40 of the present invention operates much like a conventional penetrometer but with compressed air or any other nonreactive gas being injected into the interior of the string 13 of hollow penetrometer push rods 12. The string 13 may be formed in sections or individual push rods 12. Exit ports 30 are located near the distal end 18 of the lowermost section 12 of the string 13. The instrument section 16, the friction sleeve 21 and the tip 20 are coupled to the string, as illustrated.

In the embodiment illustrated, a sealed chamber 50 is formed between a pair of welded circular plates 52 and 54 which are located in confronting relationship on opposite sides of the exit ports 30 within the hollow push rod 12. The plate 52 has an inlet 56 which is sealably coupled to air line 57. Further, plates 52 and 54 have axially aligned apertures 58 and 60 for receiving the instrument cable 22 therein. The apertures 58 and 60 may be sealed with an appropriate O-ring or grommet 62 so as to confine pressurized air within the chamber 50. Air entering the chamber 50 flows out of the exit ports 30 and upwardly along the string 13 (see the arrows 59). The air 59 provides lubrication between the outer walls of the penetrometer string 13 and the soil 11. The air flows upwardly only and does not interfere in any way with the instrument housing 16, the friction sleeve 21, or the tip 20.

Figure 3A:
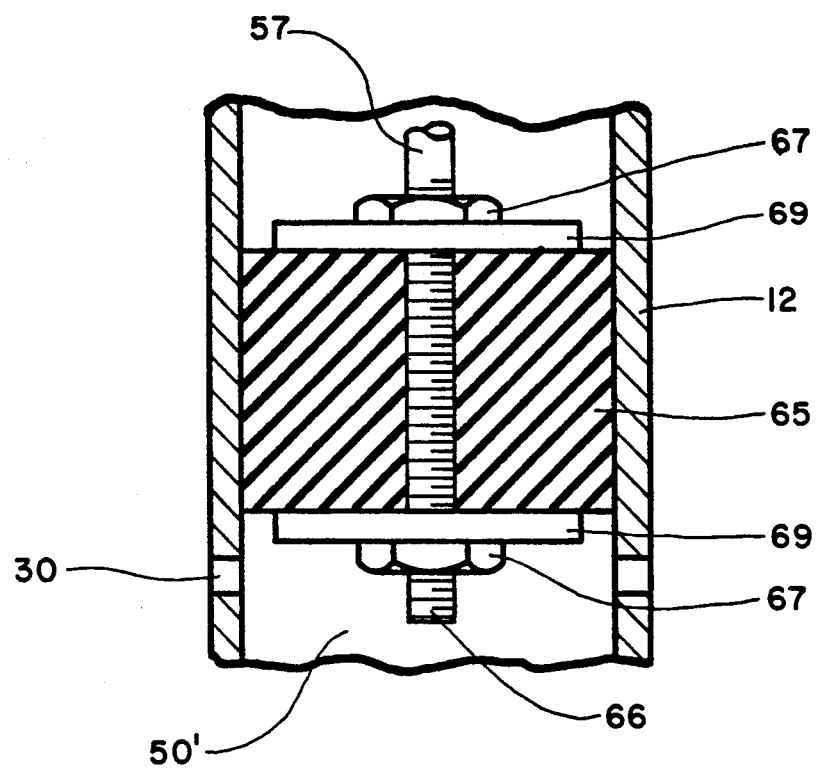
FIG. 3A is yet another embodiment for introducing gaseous fluid into the string of push rods.
Figure 3:
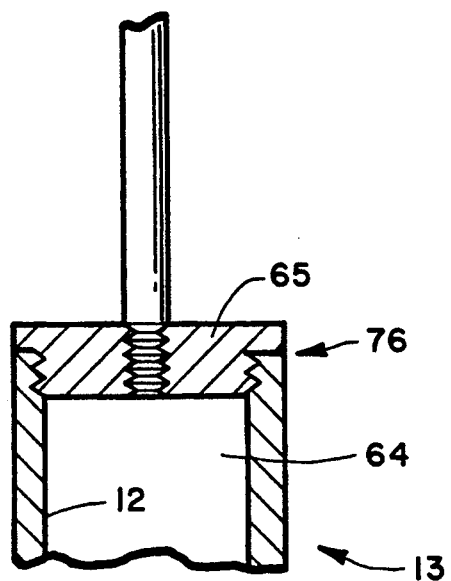
FIG. 3 is a detail of an alternative embodiment of the invention for introducing gaseous fluid into the drill string.

In an alternative embodiment, the interior 64 of the individual interconnected sections of the hollow push rods 12 may be pressurized without a separate air line by means of an air fitting 65 at the upper end 76 of the rod 12 as shown in FIG. 3. In accordance with this embodiment, lubricating air is directly supplied to the exit ports 30 via the interior of the push rod string 13. However, in some soil configurations, especially where ground water is encountered, it is preferred to provide the air line 58. In particular, it is often preferred to employ a check valve 66 in the air line 57 for preventing fluids from backing up into the chamber 50. It may also be desirable to use an air line so that the pressurization of the string 13 is not required as each section of push rod 12 is added thereto. In some arrangements, the air line is pre-threaded through a number of rods 12 and they are added to the string as required.

FIG. 3A illustrates another embodiment of the invention in which an apertured plug formed of resilient material is secured to the lower end of the air line 57 near the ports 30. The air line 57 has a threaded portion 66 and the plug 65 is axially compressed between a pair of compression nuts 67 which bear against opposed washers 69. In accordance with the embodiment illustrated in FIG. 3A, a gas tight chamber 50 is formed in the pipe or rod section 12 adjacent the exit ports 30.

Figure 4:
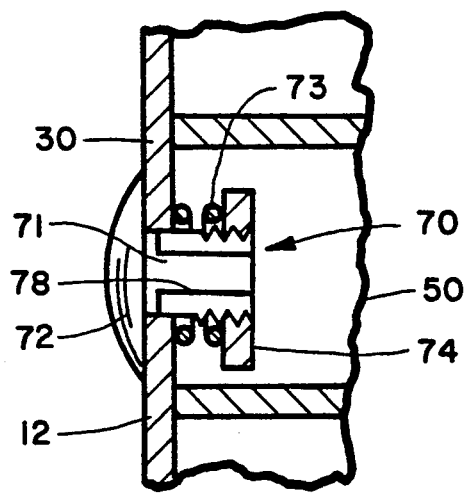
FIG. 4 is a detail of a check valve in an exit port.

If desired, each of the ports 30 may have an individual check valve 70. In an exemplary alternative arrangement, illustrated in FIG. 4, each of the ports 30 may have an individual check valve 70. Each check valve 70 has a body 71 formed with a cap 72, which is normally urged against the outside wall of the push rod 12, and a tail 74, which engages the inside wall of the rod 12 and acts as a stop when air pressure builds up inside the chamber 50. Spring 73, captured between the inside wall and the tail 74 normally urges the valve 70 closed. Pressure within the string urges the valve 70 outwardly. A passageway 78 in the form of openings in the valve body 71 allows the escape of air under pressure to the exterior of the push rod 12. In the event that ground water is present in the vicinity of the gas exits parts 30, in the absence of air pressure, back flow is prevented because the cap 72 is urged against the rod 12 by the spring 73 and by back pressure of the ground water thereagainst, whereby the openings 30 are closed. Other check valve arrangements may be provided as desired.

An experimental 60-degree cone penetrometer truck was fabricated. The device unit has four 1/16 inch gas holes around the rod so that compressed air or nitrogen pumped or released under pressure in the rod can be injected along the side of the rod as the rod is forced into the ground. The experimental cone was built and tested to determine if gas moving in the penetrometer hole could be used to reduce the friction between the rod and the surrounding soil and to thereby decrease the force required to push the penetrometer rod to a given depth. Reduced rod friction means that a greater depth can be reached with a given reaction mass so as to increase the maximum depth that can be reached with existing equipment without increasing its reaction mass.

An experimental gas injection cone was tested at a site underlain by Vicksburg Loess, a relatively homogenous silt and sandy silt. The test equipment available allowed gas pressure inside the rod to be maintained. The gas source used in the test was a high pressure nitrogen gas bottle equipped with a regulator that allowed the pressure to be dropped to 60 psi.

The force required to push a standard 1.45-inch rod into the ground was measured using stain gauges attached to the yoke of the ram set in the penetrometer truck. Two penetrometer pushes were made; one with the gas pressure on and one with the gas pressure off. The strain gauge readouts were zeroed prior to each push.

Figure 5:
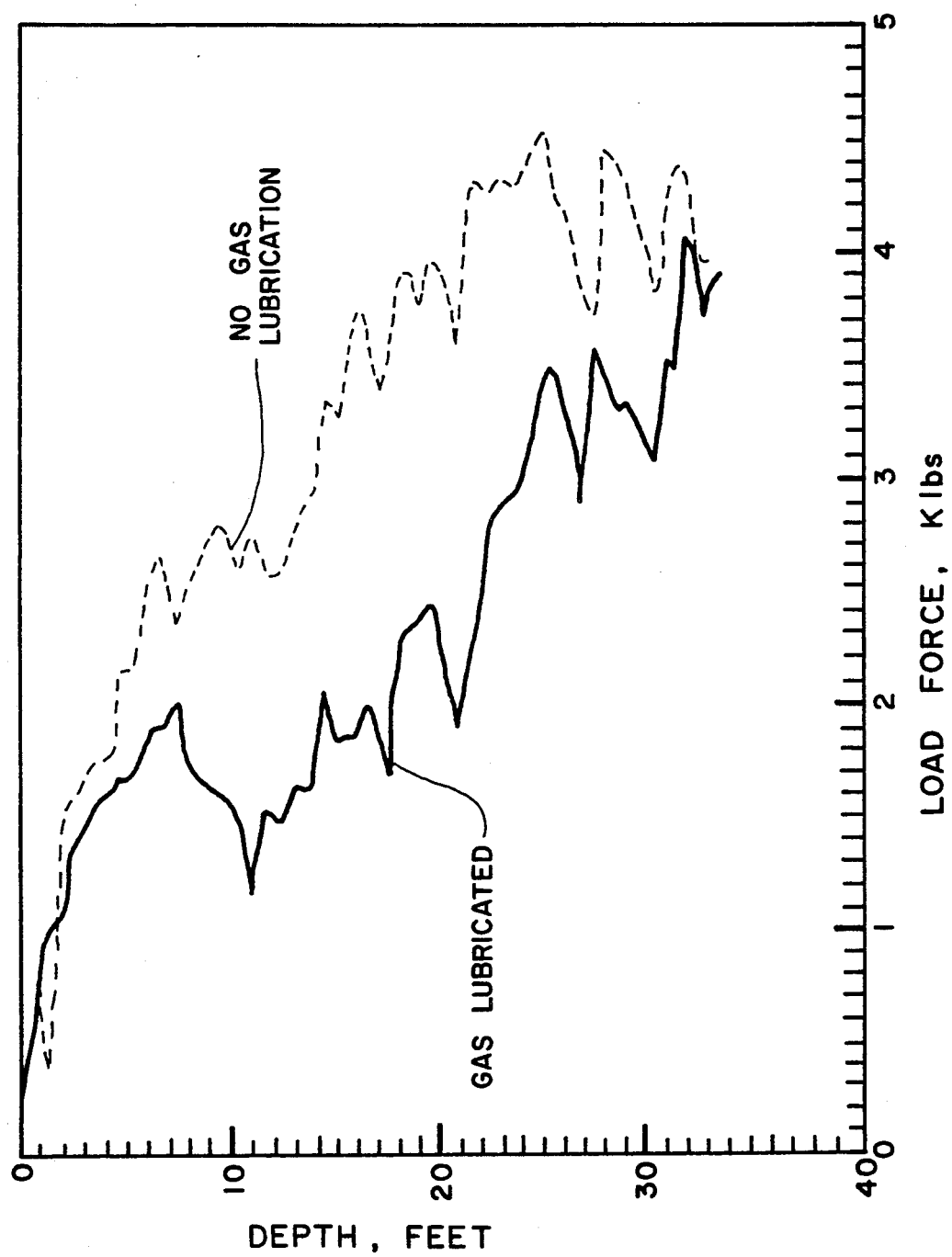
FIG. 5 is a plot of depth versus load force in which the penetration force with and without gas lubrication in accordance with the present invention is illustrated.

The depth of each point in each push is plotted against the force on the rams at that depth for both a gas-lubricated and a non-lubricated push (FIG. 5). This data shows that the force required to push to a stated depth is decreased by releasing gas into the soil around the rod. The reduction in the force needed was typically 25–30%. This result translates into a 25 to 30% increase in the depth of penetration for a given reaction force. The pattern apparent in the variation in the force on the ram suggests that the gas lubrication is most efficient in reducing the force when the rod is moving and least effective when the string is restarted after the addition of a new rod section. The pattern of pressure maxima correspond to the positions of push initiation after the new rod is added.

In accordance with the invention, a significant increase in penetration depth may be achieved. For example, in prior designs, penetration depths may have been limited to about 150 feet in normally compacted soil. By means of the present invention, the penetration distance may be increased significantly under the same circumstances. Further, in accordance with the preferred embodiment of the invention, air pressure is supplied to the chamber 50 at a pressure of 1 psi or greater per foot of depth. Such a pressure is sufficient to provide air lubrication for the penetrometer push rod string 13 and can be maintained low enough to avoid damaging the adjacent soil 11. It is also possible to provide a number of air outlets along the length of the string 13 and to size the gas exit parts 30 so as to tune the air flow along the length of the push rod.

While there have been described what at present are considered to be the preferred embodiments of the present invention, it will be readily apparent to those skilled in the art that various changes may be made therein without departing from the invention and it is intended in the claims to cover such changes and modifications as fall within the true spirit and scope of the invention.

What is claimed is:

1. An air lubricated penetrometer having a tip for penetrating soil, an instrument housing axially secured to said tip, sensor means for sensing soil conditions thereat and a penetrometer rod string having at least one push rod section axially secured to a proximate end of said means for transferring a penetration force axially to said penetrometer tip and through said instrument housing;
    means for introducing a gaseous fluid into said penetrometer rod, a distal end of said penetrometer rod having a plurality of gas exit ports for permitting the passage of said gaseous fluid to exit said penetrometer rod at said distal end of said string proximate said instrument housing lubricating only said rod string upstream of said penetrometer tip and instrument housing.

2. The air lubricated penetrometer of claim 1, wherein each push rod is a hollow tubular section of pipe and an instrument cable coupled to said instrument housing is threaded therethrough.

3. The air lubricated penetrometer of claim 1, further including a check valve located in said means for introducing a gaseous fluid.

4. The air lubricated penetrometer of claim 1, wherein a chamber is formed in a distal end of said string adjacent to two apertures, said chamber having an inlet within the string, said apertures forming an outlet of the chamber.

5. The air lubricated penetrometer of claim 4, wherein said chamber is formed between an interior wall of said string and a pair of plates in confronting relationship on opposite sides of said exit ports where the plates are sealingly secured to the interior walls of said string.

6. The air lubricated penetrometer of claim 5, wherein one of said plates has an aperture forming the inlet of said chamber.

7. The air lubricated penetrometer of claim 6, wherein the gaseous fluid is supplied at pressure of about 1 psi per foot of string.

8. The air lubricated penetrometer of claim 1, further including a check valve formed in each of said gas exit ports for preventing back flow of substances from outside of the string into the string.

9. The air lubricated penetrometer of claim 1, wherein the gaseous fluid is a nonreactive gas including air and said gaseous fluid flows upwardly and about the string.

10. The air lubricated penetrometer of claim 1, further including an axial support for securing the penetrometer tip to a distal end of the instrument housing.

11. The air lubricated penetrometer of claim 10, further including a friction sleeve surrounding the axial support between the penetrometer tip and the instrument housing.

12. The air lubricated penetrometer of claim 1, wherein an apertured plug is located at the proximal end of said string, said plug having a through hole therein for receiving the gaseous fluid therethrough in communication with said gas exit ports.

13. The air lubricated penetrometer of claim 12, wherein the plug comprises a resilient member having side walls conforming to the interior of the rod and opposite axial end faces;
    a hollow threadable member is located in said hole and fastener means engage the threaded member at opposite faces for axially compressing the plug to sealingly engage the plug with the interior of the rod.

* * * * *